(12) United States Patent
Komplin et al.

(10) Patent No.: US 7,381,852 B2
(45) Date of Patent: Jun. 3, 2008

(54) PROCESS FOR HYDROGENATING AN ALDEHYDE

(75) Inventors: Glenn Charles Komplin, Katy, TX (US); John Anthony Smegal, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 11/734,194

(22) Filed: Apr. 11, 2007

(65) Prior Publication Data

US 2007/0249872 A1    Oct. 25, 2007

Related U.S. Application Data

(60) Provisional application No. 60/791,774, filed on Apr. 13, 2006.

(51) Int. Cl.
  *C07C 29/14* (2006.01)
(52) U.S. Cl. .................. 568/862; 568/880; 568/881; 568/882; 568/883
(58) Field of Classification Search ................ 568/862, 568/881, 880, 882, 883
  See application file for complete search history.

(56) References Cited

U.S. PATENT DOCUMENTS

| | | | |
|---|---|---|---|
| 2,434,110 A | 1/1948 | Hatch et al. .............. 260/602 |
| 3,068,303 A | 12/1962 | Pattison ...................... 260/677 |
| 3,098,882 A | 7/1963 | Arnold ....................... 260/677 |
| 3,109,804 A | 11/1963 | Martin ........................ 208/89 |
| 3,205,281 A | 9/1965 | Fleming et al. ............ 260/683 |
| 3,260,759 A | 7/1966 | Skinner ..................... 260/635 |
| 3,296,325 A | 1/1967 | Gross et al. ................ 260/677 |
| 4,912,260 A | 3/1990 | Dobson et al. ............. 564/480 |
| 5,015,789 A | 5/1991 | Amtz et al. ................ 568/862 |
| 5,093,537 A | 3/1992 | Unruh et al. ............... 568/862 |
| 5,210,318 A | 5/1993 | Briggs et al. .............. 568/496 |
| RE34,349 E | 8/1993 | Unruh et al. ............... 568/862 |
| 5,256,827 A | 10/1993 | Slaugh et al. .............. 568/454 |
| 5,334,778 A | 8/1994 | Haas et al. ................. 568/862 |
| 5,358,633 A | 10/1994 | Dai et al. ................ 208/216 R |
| 5,364,984 A | 11/1994 | Amtz et al. ................ 568/862 |
| 5,382,715 A * | 1/1995 | Vargas et al. .............. 568/882 |
| 5,389,595 A | 2/1995 | Simpson et al. ........... 502/315 |
| 5,399,793 A * | 3/1995 | Vargas et al. .............. 568/883 |
| 5,449,653 A | 9/1995 | Briggs et al. .............. 502/166 |
| 5,773,657 A | 6/1998 | Rütter et al. ............... 564/450 |
| 5,786,524 A | 7/1998 | Powell et al. .............. 568/862 |
| 5,814,112 A | 9/1998 | Elliott et al. .............. 48/197 R |
| 5,817,594 A | 10/1998 | McNamara et al. ........ 502/313 |
| 5,888,380 A | 3/1999 | Fujita et al. ............ 208/251 H |
| 5,910,241 A | 6/1999 | McNamara et al. .... 208/251 H |
| 5,916,838 A | 6/1999 | Wulff-Döring et al. ..... 502/326 |
| 5,936,126 A | 8/1999 | Rühl et al. ................. 564/451 |
| 5,945,570 A | 8/1999 | Arhancet et al. ........... 568/862 |
| 5,958,825 A | 9/1999 | Wulff-Döring et al. ..... 502/300 |
| 5,977,013 A | 11/1999 | Elliott et al. ............... 502/337 |
| 6,152,975 A | 11/2000 | Elliott et al. .............. 48/197 R |
| 6,232,511 B1 | 5/2001 | Haas et al. ................. 568/862 |
| 6,342,464 B1 | 1/2002 | Arhancet et al. ........... 502/257 |
| 6,376,720 B1 | 4/2002 | Han .......................... 568/483 |
| 6,399,538 B1 | 6/2002 | Hucul ....................... 502/325 |
| 6,429,167 B1 | 8/2002 | Maeno et al. .............. 502/325 |
| 6,670,300 B2 | 12/2003 | Werpy et al. .............. 502/182 |
| 6,911,566 B2 | 6/2005 | Tsunoda et al. ............ 568/862 |
| 2002/0087036 A1 | 7/2002 | Haas et al. ................. 568/885 |
| 2004/0097764 A1 | 5/2004 | Tsunoda et al. ............ 568/860 |
| 2004/0182749 A1 | 9/2004 | Domokos et al. ........... 208/213 |
| 2004/0225161 A1 | 11/2004 | Sunkara et al. ............ 568/852 |
| 2004/0260125 A1 | 12/2004 | Seapan et al. .............. 568/868 |
| 2005/0033099 A1 | 2/2005 | Ryu et al. .................. 585/259 |
| 2005/0080300 A1 | 4/2005 | Komplin et al. ........... 568/862 |

FOREIGN PATENT DOCUMENTS

| | | |
|---|---|---|
| CN | 1342521 A | 4/2002 |
| CN | 1342633 A | 4/2002 |
| CN | 1428190 A | 7/2003 |
| CN | 1428322 A | 7/2003 |
| CN | 1122568 C | 10/2003 |
| EP | 0906258 | 3/2002 |
| FR | 2191939 | 8/1974 |
| GB | 829475 | 3/1960 |
| GB | 1011270 | 3/1963 |
| GB | 966270 | 8/1964 |
| GB | 1436458 | 5/1976 |
| GB | 1581379 | 12/1980 |
| JP | 54084508 | 12/1977 |
| JP | 83049532 | 12/1977 |
| JP | 2004182622 | 7/2004 |
| WO | WO0000456 | 1/2000 |
| WO | WO2006116193 A1 | 11/2006 |

OTHER PUBLICATIONS

"The Heterogeneous Oxidation of Hydrogen Sulfide at Concentrations Below 1000 ppm in Nitrogen/Air Mixtures Over Supported Metal Oxide Catalysts," W. G. Cook & R. A. Ross, Atmospheric Environment, (1967-1969) 7(2) pp. 145-151 Pergamon Press (1973).

(Continued)

*Primary Examiner*—Elvis O. Price

(57) ABSTRACT

The present invention relates to a process for hydrogenating an aldehyde. An aldehyde is contacted with a catalyst comprising a support containing at least 95% α-alumina and non-support metals dispersed on the surface of the support. The non-support metals comprise nickel and/or one or more compounds thereof and molybdenum and/or one or more compounds thereof. The nickel and/or one or more compounds thereof comprise from 3 wt. % to 9 wt. % of the catalyst, by metallic weight, and the molybdenum and/or one or more compounds thereof comprise from 1 wt. % to 4 wt. % of the catalyst, by metallic weight.

22 Claims, No Drawings

OTHER PUBLICATIONS

"Effects of Small $MoO_3$ Additions on the Properties of Nickel Catalysts for the Steam Reforming of Hydrocarbons II. Ni-Mo/$Al_2O_3$ catalysts in Reforming, Hydrogenolysis and Cracking of n-butane," T. Borowiecki, G. Giecko, M. Panczyk, Applied Catalysis A: General 230 (2002) pp. 89-97.

Oxidacion Deshidrogenante De Etilbenceno a Estireno Sobre Oxidos De Molibdeno Y Niquel, H. Kum & J. L. Seoane, Anales De Quimica (1968-1979) 72(7-8), pp. 703-708 (1976) Abstract).

37 Modification of 3-Hydroxyproanal Hydrogenatioan Catalyst, Z. Xu, S. Guo, J. Xie, C. Gu, & P. Wang, Shiyou Huagong, 92005 34(2), pp. 132-135 (Abstract) (2005).

* cited by examiner

PROCESS FOR HYDROGENATING AN ALDEHYDE

This application claims the benefit of the priority date of U.S. Provisional Application Ser. No. 60/791,774 filed Apr. 13, 2006.

FIELD OF THE INVENTION

The present invention relates to a process for hydrogenating an aldehyde. More particularly, the present invention relates to a process for hydrogenating an aldehyde by contacting the aldehyde with a catalyst in the presence of hydrogen, where the catalyst is comprised of a support containing at least 95% α-alumina, and non-support metals comprising nickel and/or one or more compounds thereof and molybdenum and/or one or more compounds thereof.

BACKGROUND OF THE INVENTION 1,3-propanediol (PDO) is a compound having multiple uses. It is used as a monomer unit in the production of polyesters and polyurethanes that are useful as films and as fibers for carpets and textiles. It is also useful as an engine coolant.

PDO may be prepared from ethylene oxide (EO) in a process involving two primary reactions. First, EO and synthesis gas ($H_2$/CO) are catalytically hydroformylated to form 3-hydroxypropionaldehyde (HPA) in an organic solvent. The HPA is extracted from the solvent with water to form an aqueous solution of HPA, and the aqueous solution of HPA is then hydrogenated to form PDO.

The hydrogenation of HPA to PDO is performed using a hydrogenation catalyst. The hydrogenation catalyst should desirably have several features: 1) it should be highly active over an extended period of time; 2) it should cause the hydrogenation to be highly selective to the formation of PDO, rather than other compounds; 3) it should have a long catalyst life; 4) it should not be discharged into the PDO product stream; and 5) it should be economically cost effective, preferably using inexpensive components and, if required, as few expensive components as possible.

According to Hatch et al., U.S. Pat. No. 2,434,110, especially preferred catalysts for hydrogenating HPA to PDO are Raney nickel and Adkin's copper-chromium oxide. Hatch et al. also disclose that other suitable catalysts for hydrogenating HPA to PDO include catalytically active compounds of metals such as Fe, Co, Cu, Pd, Zr, Ti, Th, V, Ta, Ag, Mo, and Al. Slurry catalysts such as Raney nickel are known to have high activity and selectivity in converting HPA to PDO as a result of the homogeneous distribution of the catalyst in the hydrogenation reaction mixture. Suspended or slurry catalysts, such as Raney nickel, however, are susceptible to being discharged into the PDO product stream in the form of soluble compounds, necessitating additional steps to purify the PDO product stream.

Haas et al., U.S. Pat. No. 6,232,511, discloses that a supported ruthenium catalyst is useful in the hydrogenation of HPA to PDO, and avoids the problem of the metallic portion of the catalyst polluting the PDO product stream. Use of the supported ruthenium catalyst in a fixed-bed is preferred. Ruthenium and other noble metals such as platinum or palladium, however, are very expensive, and ruthenium and other noble metal based catalysts are not commercially attractive, especially for large scale continuous operations.

Arhancet et al. U.S. Pat. Nos. 5,945,570 and 6,342,464, disclose a hydrogenation catalyst for hydrogenating HPA to PDO that is a bulk metal catalyst. The bulk metal catalyst includes 25 to 60 wt. % nickel and 5 to 20 wt. % molybdenum bound together with a binder made up of oxides of silicon, and silicates and oxides of zinc, zirconium, calcium, magnesium and/or aluminum. The catalyst is particulate and may be used in a fixed bed hydrogenation reactor such as a trickle bed reactor. Bulk metal catalysts, however, are subject to breaking into catalytic fines over an extended period of use, and may lack sufficient physical stability to be used in large scale long-term continuous operations.

In short, hydrogenation catalysts in the art formed of economically advantageous non-noble catalytic metals either do not exhibit sufficient hydrogenation activity over an extended period of time, are discharged into the product stream requiring additional steps to purify the product stream, or are not sufficiently physically stable to be utilized in an industrial scale continuous long-term aldehyde hydrogenation process.

SUMMARY OF THE INVENTION

In one aspect, the present invention provides a process for hydrogenating an aldehyde comprising contacting an aldehyde with a catalyst in the presence of hydrogen where the catalyst is comprised of a support and non-support metal components dispersed on the surface of the support, the support containing at least 95% α-alumina as measured by powder x-ray diffraction, and the non-support metal components comprise nickel and/or one or more compounds thereof and molybdenum and/or one or more compounds thereof, where the nickel and/or one or more compounds thereof comprises from 3 wt. % to 9 wt. % of the catalyst, by metallic weight, and the molybdenum and/or one or more compounds thereof comprises from 1 wt. % to 4 wt. %, by metallic weight, of the catalyst.

DETAILED DESCRIPTION OF THE INVENTION

The present invention provides a process for hydrogenating an aldehyde, particularly hydroxyaldehydes, and most particularly HPA, by contacting the aldehyde with a catalyst in the presence of hydrogen. The catalyst is a supported catalyst that is particularly useful as a fixed-bed catalyst. The catalyst includes a support containing at least 95% α-alumina that provides excellent resistance against crushing and catalyst breakdown into fines. The catalyst is selective to hydrogenation of the aldehyde relative to catalysts having more acidic supports, e.g. silicas and transition aluminas such as gamma, delta, theta, and kappa aluminas, since the relatively non-acidic α-alumina support is less likely to catalyze the formation of acetals from the aldehyde. The catalyst comprises non-support catalytically active metal components nickel and/or one or more compounds thereof and molybdenum and/or one or more compounds thereof. The non-support catalytically active metal components are dispersed on the α-alumina support. The catalyst is effective to hydrogenate an aldehyde at a commercially acceptable rate despite the relatively small total quantity of catalytically active metal components that can be loaded on the α-alumina support—even though the metal components are not required to include highly active hydrogenation catalytic noble metals such as ruthenium, platinum, or palladium. The catalyst of the present invention provides significant economic advantage over other aldehyde, and particularly HPA, hydrogenation catalysts since relatively small amounts of relatively inexpensive active catalyst metal components are required to provide long-term hydrogenation activity at relatively high hydrogenation rates, and the catalyst has a long life due to its physical stability in combination with its long-term catalytic activity.

In the process of the present invention, a feed comprising an aldehyde is contacted with hydrogen and a hydrogenation catalyst in a hydrogenation reactor, the catalyst comprising a support and non-support metal components located on the support, to hydrogenate the aldehyde to an alcohol, diol, triol, or polyol. The catalyst support is comprised of at least 95% α-alumina as measured by powder x-ray diffraction. The catalyst non-support metal components are nickel and/or one or more compounds thereof, and molybdenum and/or one or more compounds thereof.

The aldehyde may be any aldehyde that may be hydrogenated to an alcohol, diol, triol, or polyol. In one embodiment, the aldehyde may be a straight or branched chain aliphatic aldehyde. In an embodiment, the straight or branched chain aliphatic aldehyde may comprise at most 8 carbon atoms, or may contain from 2 to 6 carbon atoms.

In an embodiment, the aldehyde is a 3-hydroxyaldehyde, i.e. a compound of the general formula

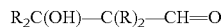
$R_2C(OH)-C(R)_2-CH=O$ wherein each R independently may be a hydrogen atom or may jointly) be a hydrocarbon group that is substituted or unsubstituted, and/or aliphatic or aromatic. Each group R may independently vary in size, for instance, from 1 to 20 carbon atoms, preferably from 1 to 10 carbon atoms. In addition, they may bear one or more substituents selected from hydroxyl, alkoxy, carbonyl, carboxy, amino, cyano, mercapto, phosphino, phosphonyl, and or silyl groups, and/or one or more halogen atoms. Preferred 3-hydroxyaldehydes are those having in total from 3 to 12 carbon atoms, and more preferably from 3 to 8 carbon atoms. Most preferably the 3-hydroxyaldehyde is HPA, i.e. wherein each R is a hydrogen atom.

The feed may be a solution containing the aldehyde where the solution may be an aqueous solution comprising at least 50 wt. %, or at least 70 wt. %, or at least 90 wt. %, or at least 95 wt. % water based on the weight of the aqueous feed solution, or an organic solution comprising at least 50 wt. %, or at least 70 wt. %, or at least 90 wt. %, or at least 95 wt. % of one or more organic solvents based on the weight of the organic feed solution. The aldehyde is preferably soluble in the feed solution, e.g. if the feed solution is aqueous the aldehyde is preferably soluble in the aqueous feed solution, and if the feed solution is organic the aldehyde is preferably soluble in the organic feed solution. In an embodiment, the aldehyde may be subject to dehydration under conditions for hydrogenating the aldehyde, and the feed solution may contain at least 1 wt. %, or at least 5 wt. %, or at least 20 wt. %, or at least 70 wt. % of water, where the water may inhibit dehydration of the aldehyde under hydrogenation conditions.

The feed solution may contain at least 0.1 wt. % of the aldehyde, at least 0.2 wt. % of the aldehyde, at least 0.3 wt. % of the aldehyde, at least 0.5 wt. % of the aldehyde, or at least 1 wt. % of the aldehyde based on the liquid weight of the feed solution. The feed solution may contain at most 15 wt. % of the aldehyde, at most 12 wt. % of the aldehyde, at most 10 wt. % of the aldehyde, or at most 8 wt. % of the aldehyde based on the liquid weight of the feed solution. The feed solution may contain from 0.1 wt. % to 15 wt. % of the aldehyde, from 0.2 wt. % to 10 wt. % of the aldehyde, or from 0.3 wt. % to 8 wt. % of the aldehyde based on the liquid weight of the solution.

If the aldehyde is present in the feed solution in an amount greater than 15 wt. %, or greater than the desired amount within the ranges set forth above, the feed solution may be diluted with solvent to obtain the desired concentration of aldehyde. For example, if the aldehyde is HPA in an aqueous solution at a concentration of greater than 15 wt. %, the aqueous solution may be diluted to the desired concentration by the addition of an aqueous liquid, e.g. water or aqueous PDO. It may be desirable to dilute the feed solution to reduce the concentration of the aldehyde in order to reduce the likelihood of formation of undesirable byproducts.

In an embodiment, the feed is a solution comprising the aldehyde, where the feed may comprise the product of an oxirane hydroformylation reaction or an aqueous extract of the product of an oxirane hydroformylation reaction. The oxirane hydroformylation reaction product may be formed by reacting an oxirane with syngas in a solvent in the presence of a hydroformylation catalyst, for example a cobalt or a rhodium based hydroformylation catalyst. The oxirane may be, for example, ethylene oxide. The solvent may be, for example, an alcohol or an ether of the formula

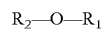
$R_2-O-R_1$ in which $R_1$ is hydrogen or a $C_{1-20}$ linear, branched, cyclic, or aromatic hydrocarbyl or a mono- or polyalkylene oxide. Preferred hydroformylation solvents include, for example, methyl-t-butyl ether, ethyl-t-butyl ether, diethyl ether, phenylisobutyl ether, ethoxyethyl ether, diphenyl ether, phenylisobutyl ether, ethoxyethyl ether, and diisopropyl ether. Blends of solvents such as tetrahydrofuran/toluene, tetrahydrofuran/heptane, and t-butylalcohol/hexane may also be used as the hydroformylation solvent. The syngas (i.e. synthesis gas) may comprise a mixture of $H_2$ and carbon monoxide having an $H_2$:CO ratio of at least 0.5:1 or at least 1:1 and at most 10:1 or at most 5:1. The syngas may be obtained from a commercially available source, or may be derived, for example, from a conventional water-gas shift reaction process.

In an embodiment, the feed may be an aqueous extract of an oxirane hydroformylation reaction mixture that contains the aldehyde. The aqueous extractant used to extract the oxirane hydroformylation reaction mixture may be water, and an optional miscibilizing agent. In an embodiment, the amount of water used to extract the oxirane hydroformylation reaction mixture may generally be an amount sufficient to provide a water:reaction mixture volume ratio of from 1:1 to 1:20, or from 1:5 to 1:15. In an embodiment, the aqueous extraction may be carried out at a temperature of from 25° C. to 55° C. In an embodiment, the aqueous extraction may be carried out under 0.34 MPa (50 psig) to 1.37 MPa (200 psig) carbon monoxide partial pressure to maximize retention of hydroformylation catalyst in the hydroformylation reaction mixture and minimize extraction of the hydroformylation catalyst into the aqueous extractant.

In an embodiment, the aqueous extractant comprising the feed containing the aldehyde may include some metal of the hydroformylation catalyst, which may be, for example, a water soluble species of cobalt or rhodium. The aqueous extract containing an aldehyde and hydroformylation catalyst may be used as the feed for the hydrogenation without removing the hydroformylation catalyst metal species.

Alternatively, in another embodiment, the hydroformylation catalyst may be oxidized and removed from the feed, either a hydroformylation reaction mixture or an aqueous extract of a hydroformylation mixture, prior to hydrogenating the aldehyde in the feed. The hydroformylation catalyst may be oxidized, for example, by passing an oxidizing gas, e.g. air or oxygen, through the feed to oxidize the metal of the hydroformylation catalyst. The oxidized metal may be removed from the feed, for example, by contacting the feed with an acid ion exchange resin. The acid ion exchange resin may be a strong acid ion exchange resin or a weak acid ion exchange resin.

In an embodiment, carbon monoxide may be stripped from the hydroformylation reaction mixture or aqueous extract of the hydroformylation reaction mixture containing the aldehyde prior to using either as a feed for hydrogenating the aldehyde. Carbon monoxide may poison the hydrogenation catalyst during hydrogenation, and is preferably removed from the feed containing the aldehyde prior to contact with the hydrogenation catalyst. Carbon monoxide may be removed from the hydroformylation reaction mixture or the aqueous extract of the hydroformylation reaction mixture by adjusting the pressure on the reaction mixture or aqueous extract to near atmospheric pressure and passing a stripping gas through the reaction mixture or aqueous extract to remove carbon monoxide from the reaction mixture or aqueous extract. The stripping gas may be air, oxygen, nitrogen, and/or a light hydrocarbon such as methane or natural gas.

Most preferably, the feed may be an aqueous extract of an ethylene oxide hydroformylation reaction mixture, where the feed comprises HPA. The ethylene oxide hydroformylation reaction mixture may be formed by hydroformylating ethylene oxide with syngas in a methyl-t-butyl ether solvent in the presence of a cobalt carbonyl or rhodium carbonyl catalyst to produce HPA. The feed may be produced by extracting the ethylene oxide hydroformylation reaction mixture with water or an aqueous solution. In an embodiment the hydroformylation reaction mixture may be extracted with water or an aqueous solution under a carbon monoxide pressure of from 0.34 MPa (50 psig) to 1.37 MPa (200 psig) to minimize extraction of the hydroformylation catalyst into the aqueous extractant that forms the feed. In an embodiment, the aqueous extract feed containing the HPA may be stripped of carbon monoxide by depressurizing the aqueous extract and passing a stripping gas through the aqueous extract, where the stripping gas may be a light hydrocarbon, oxygen, air, and/or nitrogen. In an embodiment, residual hydroformylation catalyst may be removed from the aqueous extract feed containing the HPA by passing an oxidizing gas such as air or oxygen through the aqueous extract to oxidize the residual hydroformylation catalyst, then passing the aqueous extract through an acid ion exchange resin.

The aldehyde in the feed is reacted with hydrogen in the presence of the catalyst using methods known in the art. A fixed-bed hydrogenation reactor is preferred for conducting the hydrogenation on an industrial scale with the catalyst used in the process of the invention. In such a reactor, the liquid reaction mixture flows or trickles over the catalyst in a fixed-bed together in the presence of hydrogen. To ensure good distribution of the hydrogen in the reaction mixture and uniform distribution of the gas/liquid mixture over the entire cross-section of the fixed bed, the liquid reaction mixture and hydrogen may be passed together through static mixers before being passed through the catalyst bed.

In the process of the present invention, hydrogen is provided for contact with the aldehyde and the hydrogenation catalyst to hydrogenate the aldehyde in the feed. In an embodiment, hydrogen may be provided in an amount in excess of the amount necessary to convert all of the aldehyde in the feed. In an embodiment, hydrogen is provided at a hydrogen partial pressure of at least 1 MPa, or at least 2 MPa, or at least 4 MPa, or at least 5 MPa. In an embodiment, hydrogen is provided at a hydrogen partial pressure of at most 70 MPa, or at most 20 MPa, or at most 10 MPa. In an embodiment, hydrogen is provided at a hydrogen partial pressure of from 1 MPa to 70 MPa, or from 2 MPa to 20 MPa, or from 4 MPa to 10 MPa.

The feed comprising an aldehyde may be contacted with hydrogen and the hydrogenation catalyst to hydrogenate the aldehyde in the feed at a pH effective to selectively promote hydrogenation of the aldehyde. The feed containing the aldehyde may have a pH, or may be adjusted to a pH, at which the aldehyde may be inhibited from converting to undesirable byproducts, for example, acetals. The initial feed solution containing the aldehyde may also have a pH, or may be adjusted to a pH, at which the aldehyde may be efficiently converted in the hydrogenation reaction. Preferably the initial feed solution containing the aldehyde may have a pH, or may be adjusted to a pH, at which the aldehyde may be efficiently converted in a hydrogenation reaction and at which the aldehyde may be inhibited from converting to undesirable byproducts.

In one embodiment, the aldehyde may be contacted with hydrogen and the hydrogenation catalyst at a pH of at least 2.0, at least 3.0, or at least 4.0 to hydrogenate the aldehyde. In one embodiment, the aldehyde may be contacted with hydrogen and the hydrogenation catalyst at a pH of at most 7.0, at most 6.5, at most 6.0, or at most 5.5 to hydrogenate the aldehyde. In one embodiment, the aldehyde may be contacted with hydrogen and the hydrogenation catalyst at a pH of from 2.0 to 7.0, from 3.0 to 6.5, from 4.0 to 6.0, or from 4.0 to 5.5 to hydrogenate the aldehyde. In an embodiment, the pH of the hydrogenation reaction mixture changes little during the reaction, and selecting or adjusting the pH of the initial feed comprising the aldehyde is effective to determine the pH at which the aldehyde is contacted with hydrogen and the hydrogenation catalyst during the course of the hydrogenation reaction.

The temperature of the mixture of hydrogen, hydrogenation catalyst, and the feed containing the aldehyde (the "reaction mixture") may be controlled within a desired range to hydrogenate the aldehyde. In an embodiment of the present invention, the reaction mixture is treated at a temperature of at least 40° C., at least 50° C. or at least 60° C. and a temperature of at most 190° C., at most 180° C., or at most 170° C. to hydrogenate the reaction mixture. In an embodiment of the invention the reaction mixture is treated at a temperature of from 40° C. to 190° C., or a temperature of from 50° C. to 180° C., or a temperature of from 60° C. to 170° C. to hydrogenate the reaction mixture.

In an embodiment of the invention, the hydrogenation is conducted in two or more hydrogenation stages where a first hydrogenation stage has a first temperature, and each subsequent hydrogenation stage has a respective temperature that is higher than the preceding hydrogenation stage. The hydrogenation stages may occur in and be located in separate hydrogenation reactors, separate hydrogenation zones in a single hydrogenation reactor, or a single hydrogenation zone in a hydrogenation reactor where the temperature in the single hydrogenation zone is raised in accordance with a predetermined sequence while retaining the reaction mixture within the single hydrogenation zone.

In one embodiment the reaction mixture containing the aldehyde, hydrogen and the hydrogenation catalyst is hydrogenated in a first hydrogenation stage having a temperature of from 40° C. to 90° C., alternatively from 50° C. to 85° C., until at least 40%, or at least 50%, or at least 60%, or at least 70%, or at least 80%, or at least 85%, or at least 95% of the aldehyde is converted. Subsequent to the first hydrogenation stage, the reaction mixture may be hydrogenated in a second hydrogenation stage having a temperature of from 50° C. to 120° C., alternatively from 60° C. to 110° C., where the temperature of the second hydrogenation stage is higher than the temperature of the first hydrogenation stage. The reaction mixture may be hydrogenated in the second stage until at least 70%, or at least 80%, or at least 90%, or at least 95%, or at least 99.5% of the aldehyde is converted. Such a stepped temperature hydrogenation is believed to inhibit the production of byproducts such as acetals by limiting the temperature of the hydrogenation reaction when high concentrations of the aldehyde are present.

In an embodiment of the invention, the reaction mixture may be hydrogenated in a third hydrogenation stage having a temperature of from 120° C. to 190° C., alternatively from 130° C. to 180° C., subsequent to hydrogenation of the reaction mixture in the second hydrogenation stage where the temperature of the third hydrogenation stage is higher than the temperature of the second hydrogenation stage. Hydrogenation of the reaction mixture in the third hydrogenation stage may be effective to convert at least 98% or at least 99% or at least 99.9% of the aldehyde and also may be effective to revert byproduct acetals to desired product. For example, when the aldehyde in the reaction mixture is 3-hydroxypropionaldehyde, the acetal formed by combination of 3-hydroxypropionaldehyde and its hydrogenation product 1,3-propanediol may be reverted to 1,3-propanediol and 3-hydroxypropionaldehyde, and the 3-hydroxypropionaldehyde may then be hydrogenated to 1,3-propanediol.

In another embodiment of the invention, the nickel-molybdenum α-alumina supported catalyst, as described herein, may be used as a catalyst to convert acetals to an alcohol containing material such as an alcohol, diol, triol, or polyol product by contacting the acetal with the catalyst in the presence of hydrogen. An acetal may be converted to an alcohol containing material by first being converted to an aldehyde and an alcohol under hydrogenation conditions, and second, contacting the resulting aldehyde with the catalyst in the presence of hydrogen to form an alcohol, where the alcohol containing material may contain the alcohol derived from the conversion of the acetal to an aldehyde and an alcohol and the alcohol derived from hydrogenation of the resulting aldehyde.

In an embodiment the nickel-molybdenum α-alumina supported catalyst may be used in a second or subsequent hydrogenation stage to revert acetals in a hydrogenation reaction product derived from one or more prior hydrogenation stages in which a different conventional hydrogenation catalyst is used to hydrogenate an aldehyde to the alcohol, diol, triol, or polyol product. For example, a conventional hydrogenation catalyst such as a Raney nickel catalyst or a supported catalyst utilizing Pt and/or Ru as active metals on a support such as carbon, $Al_2O_3$, $SiO_2$ or $TiO_2$ may be utilized to hydrogenate a reaction mixture containing an aldehyde in a first hydrogenation stage at temperatures up to 120° C., and the nickel-molybdenum α-alumina supported catalyst may be used to hydrogenate the reaction mixture from the first hydrogenation stage in a second hydrogenation stage at temperatures of from 120° C. to 190° C. to revert acetals and convert remaining aldehyde to product.

The hydrogenation catalyst used in the process of the present invention comprises a support and non-support metal components dispersed on the surface of the support. The support comprises at least 95 wt. %, at least 96 wt. %, at least 97 wt. %, at least 98 wt. %, at least 99 wt. %, or at least 99.5 wt. % α-alumina as measured by powder x-ray diffraction, and may contain at most 99.9 wt. % α-alumina phase as measured by powder x-ray diffraction. The support may contain up to 0.6 wt. % silica as measured by x-ray fluorescence. The support of the catalyst may contain little or no other phases of alumina other than α-alumina such as gamma-alumina, eta-alumina, delta-alumina, theta-alumina, or kappa-alumina. Other forms of alumina have substantially more porosity than α-alumina, and do not provide the desired mechanical strength or chemical resistance. In a preferred embodiment, the support of the catalyst contains no other forms of alumina as measured by powder X-ray diffraction than α-alumina. In a preferred embodiment, the support of the hydrogenation catalyst consists essentially of alumina in the α-alumina phase.

The support of the catalyst has a high degree of mechanical strength and a small surface area/pore volume relative to supports utilized in conventional supported hydrogenation catalysts. The support may have few or no pores less than 500 Å in diameter, and a median pore diameter of from about 1400 Å to around 1800 Å, as measured by mercury porosimetry at a 140° contact angle. The support preferably may have a pore volume of from 0.30 ml/g to 0.50 ml/g. As used herein, pore size distribution (including median pore diameter determinations) and pore volume are defined as measured by mercury porosimetry at a 140° contact angle, an Hg surface tension of 485 dyne/cm, over a pressure range of from 14.37 to 59774 psia (0.099 to 412 MPa). Mercury porosimetry measurements may be made with an Autopore IV 9500 availiable from Micromeritics Instrument Corp.

As a result of its limited porosity, the support may have an $N_2$ BET surface area of less than 10 $m^2$/g, and preferably has an $N_2$ BET surface area of from 3 $m^2$/g to 9 $m^2$/g, and more preferably has a $N_2$ BET surface area of from 4 $m^2$/g to 7 $m^2$/g. As used herein, $N_2$ BET surface area refers to the surface area of a solid measured by the Brunauer, Emmett, and Teller method of calculation of the surface area of a solid by physical adsorption of nitrogen gas molecules, which is well known in the art. Generally, decreasing support surface area increases the mechanical strength of the support while decreasing the available area upon which to deposit the active metal components of the catalyst.

The lack of small pores provides the support with a relatively high crush strength and inhibits breakdown of the catalyst into fines over the life of the catalyst. The high crush strength of the support provides the catalyst with the strength necessary for a long catalyst life as a fixed-bed hydrogenation catalyst.

The support of the hydrogenation catalyst may have a shape, size, and structure such that the support can be placed and retained in a fixed hydrogenation bed such as a trickle bed reactor. Most preferably the support is a tri-lobal or cylindrical pellet.

The non-support active metal components of the hydrogenation catalyst deposited on the surface of the support comprise nickel and/or one or more compounds thereof and molybdenum and/or one or more compounds thereof. The nickel and/or compound(s) thereof comprises from 3 wt. % to 9 wt. % of the weight of the catalyst, by metallic weight, or from 4 wt. % to 7 wt. % of the weight of the catalyst, by metallic weight. The molybdenum and/or compound(s) thereof comprises from 1 wt. % to 4 wt. % of the weight of the catalyst, by metallic weight, or from 2 wt. % to 3 wt. % of the weight of the catalyst, by metallic weight.

The nickel and/or compound(s) thereof is preferably present in the catalyst in a weight ratio by metallic weight of at least 1:1 relative to the molybdenum and/or compound(s) thereof. In an embodiment, the nickel and/or compound(s) thereof is present in the catalyst in a weight ratio by metallic weight of from 1:1 to 3:1 relative to the molybdenum and/or compound(s) thereof.

In an embodiment, small amounts of catalytically active metal components other than nickel and molybdenum and/or their compounds may be present in the catalyst on the surface of the support as non-support metal components, and may comprise up to 1 wt. % of the catalyst, by metallic weight. In an embodiment, cobalt and/or one or more compounds thereof comprise(s) from 0.1 wt. % to 1 wt. % of the catalyst, by metallic weight. Preferably, due to the expense of noble metals, the non-support active metal components do not include the noble metals ruthenium, platinum, and palladium (i.e. ruthenium, platinum, and palladium are excluded from non-support metal components that may be utilized in the catalyst).

Preferably, the non-support active metal components of the hydrogenation catalyst consist essentially of nickel and/or one or more compounds of thereof and molybdenum and/or one or more compounds thereof. The nickel, as metallic nickel and/or one or more compounds of nickel, preferably comprises from 3 wt. % to 6 wt. % of the weight of the hydrogenation catalyst, by metallic weight. The molybdenum, as metallic molybdenum and/or one or more compounds of molybdenum, preferably comprises from 1 wt. % to 3 wt. % of the hydrogenation catalyst, by metallic weight.

The non-support active metal components may substantially increase the surface area of the finished hydrogenation catalyst relative to the surface area of the support, thereby providing more surface area than the support alone to catalytically interact to convert aldehydes in the presence of hydrogen. The surface area of the finished catalyst may be from 1.5 to 5 times the surface area of the support, or may be from 1.5 to 3 times the surface area of the support. The finished catalyst may have an $N_2$ BET surface area of from 10 $m^2/g$ to 30 $m^2/g$, or from 15 $m^2/g$ to 25 $m^2/g$.

The non-support active metal components may decrease the pore volume of the finished catalyst relative to the pore volume of the support. Typically the pore volume (Hg) of the finished catalyst may range from 0.2 cc/g to 0.35 cc/g, measured by mercury porosimetry at a 140° contact angle. The median pore diameter of the finished catalyst may range from 1300 Å to 1700 Å.

As noted above, the relatively high crush strength of the support provides the hydrogenation catalyst with strength that may inhibit the breakdown of the catalyst into fines, thereby enhancing the lifespan of the catalyst. The crush strength of the catalyst may be measured by a flat plate crush of individual catalyst pellets, and reported as the average force required to crush the pellet when placed length-wise between two flat plates per average length of the catalyst pellet. The flat plate crush strength is calculated according to the following formula:

$$\text{Side Crush Strength per Length} = \frac{\Sigma(\text{All Individual Crush Strength Measurements})}{\Sigma(\text{All Individual Length Measurements})}$$

The hydrogenation catalyst used in the process of the present invention has a high crush strength. The catalyst, when having a length of from 2 mm to 6 mm and a diameter of from 0.8 mm to 1.6 mm, may have an initial crush strength, prior to being exposed to hydrogenation conditions, of at least 2.7 kg/mm, more preferably at least 2.8 kg/mm, more preferably at least 2.9 kg/mm, and more preferably at least 3.0 kg/mm. The hydrogenation catalyst used in the process of the present invention also preferably retains its crush strength after exposure to hydrogenation conditions, where spent hydrogenation catalyst, initially having the dimensions described above, preferably has a crush strength of at least 2.3 kg/mm, more preferably at least 2.4 kg/mm, and most preferably at least 2.5 kg/mm.

The hydrogenation catalyst has substantial catalytic activity to convert the aldehyde under hydrogenation conditions, especially after an extended period of time. The catalyst may have an initial activity sufficient to catalyze hydrogenation of an aldehyde at a rate of at least 50 ml aldehyde/ml catalyst.hr at a temperature of from 50° C. to 90° C., a pH of from 4.5 to 6.0, and a hydrogen partial pressure of from 6.89 MPa to 10.68 MPa. In an embodiment of the invention, the catalyst has an activity sufficient to catalyze hydrogenation of an aldehyde at a rate of at least 30 ml aldehyde/ml catalyst.hr at a temperature of from 50° C. to 90° C., a pH of from 4.5 to 6.0, and a hydrogen partial pressure of from 6.894 MPa to 10.68 MPa after at least 24 hours exposure to the same hydrogenation conditions. In another embodiment of the invention, the catalyst has an activity sufficient to catalyze hydrogenation of an aldehyde at a rate of at least 35 ml aldehyde/ml catalyst.hr at a temperature of from 50° C. to 90° C., a pH of from 4.5 to 6.0, and a hydrogen partial pressure of from 6.89 MPa to 10.68 MPa after at least 24 hours of exposure to the same hydrogenation conditions, and preferably has an activity to catalyze hydrogenation of an aldehyde at a rate of at least 40 ml aldehyde/ml catalyst.hr under such conditions after at least 24 hours of exposure to the same hydrogenation conditions.

In an embodiment of the invention, the hydrogenation catalyst used in the process of the present invention contains no halogens. Halogens may be deposited on the support of the catalyst in the preparation of the catalyst as a metal salt with the active metal components of the catalyst. Halogens, however, are known to corrode metal components of hydrogenation reactors, so it is desirable to avoid catalysts containing halogens. If metal salts are used to prepare the catalyst of the present invention, preferably the catalyst is prepared using metal salts of the active metals that are not halide salts.

The hydrogenation catalyst used in the process of the present invention may be prepared by first preparing the support comprised of α-alumina; then depositing the non-support metal components on the support, where the non-support metal components include nickel and/or one or more compounds thereof, and molybdenum and/or one or more compounds thereof; calcining the support with the non-support metal components thereon to form a catalyst precursor; and reducing the metal of the non-support metal components of the catalyst precursor to form the catalyst.

The α-alumina support may be prepared by calcining extruded alumina pellets. The extruded alumina pellets may be produced by mulling a mixture of pseudo-boehmite precipitated alumina powder with water and acid to form an extrudable mixture. The extrudable mixture may then be extruded through shaped dies to form the pellets, which may then be dried. The extruded pellets may then be dried and then calcined at a temperature of at least 1150° C., preferably from 1250° C. to 1350° C., for at least 1 hour to form the α-alumina phase support. The calcination reduces the pore volume ($H_2O$) of the alumina pellets from above 0.8 cc/g to 0.3-0.5 cc/g, and reduces the $N_2$ BET surface area of the pellets from above 225 $m^2/g$ to below 10 $m^2/g$ while increasing the median pore diameter of the pellets from about 100 Å to about 1400-1800 Å. Preferably the calcined α-alumina pellets used as the support have a tri-lobe or cylindrical shape.

The nickel component is deposited on the support comprised of α-alumina. The nickel component should be dispersed relatively evenly over the surface of the support to ensure that the catalyst has high activity. The nickel component may be deposited on the support by any procedure that deposits a disperse desired quantity of metallic nickel onto the support. The nickel component is preferably deposited on the support by determining the water absorption capacity of the support, and loading the support in accordance with its water absorption capacity with an aqueous nickel solution that has a nickel content corresponding to the desired metallic nickel concentration in the finished catalyst—where the entire quantity of the solution is absorbed by the support. The nickel solution may be prepared to provide a concentration of nickel, by metallic weight, of 3 wt. % to 9 wt. % of the finished catalyst, or from 4 wt. % to 7 wt. % of the finished catalyst by metallic weight. In an embodiment of the invention, the nickel solution is prepared to provide a concentration of nickel, by metallic weight, of 5 wt. % of the finished catalyst.

Preferably, nickel carbonate is used in the aqueous nickel solution, although other water-soluble nickel compounds such as nickel nitrate or nickel acetate may be used either with nickel carbonate or in place of nickel carbonate in the aqueous nickel solution. Nickel halide salts may be used in the aqueous nickel solution, but are less preferred, since halides are known to be corrosive to steel components of hydrogenation reactors. Ammonium carbonate [$(NH_4)_2CO_3$] and ammonium hydroxide may be included in the aqueous nickel solution to aid in the dissolution of the nickel and/or nickel compound(s) in the aqueous solution.

The molybdenum component may also be deposited on the support with the nickel as a mixture or alloy of nickel and molybdenum. The molybdenum component may be included in a weight ratio relative to the nickel component, by metallic weight, of from 1:1 to 1:3. Preferably, the desired amount of molybdenum component is included in an aqueous base/water-soluble form in the aqueous nickel solution, which is then loaded onto the support. Molybdenum trioxide may be used in an aqueous nickel/molybdenum solution, although other aqueous base/water soluble molybdenum compounds may be used such as ammonium dimolybdate and ammonium heptamolybdate tetrahydrate.

If desired additional metal components, for example cobalt or one or more cobalt compounds, may be deposited on the support with the nickel and molybdenum. The additional metal components may be included in an amount effective to produce a catalyst containing up to 1 wt. % of the additional metal components. If cobalt is used, the desired amount of cobalt may be included in an aqueous base/water soluble form in the aqueous nickel and molybdenum solution, which is then loaded onto the support. Cobalt may be included in the aqueous nickel/molybdenum solution as cobalt carbonate.

After the support is impregnated with the nickel and molybdenum components, and other additional metal components if desired, the metal impregnated support may be aged. Preferably the metal impregnated support is aged at room temperature for a period of from 1 hour to 3 hours, most preferably for a period of 2 hours.

The metal impregenated support may then be dried and calcined to form a catalyst precursor. The metal impregnated support may be dried at a temperature of from 25° C. to 250° C. for a period of from 1 hour to 4 hours, and most preferably at a temperature of 150° C. for a period of 3 hours. After the metal impregnated support is dry, it may be calcined at a temperature of from 350° C. to 500° C. for a period of from 30 minutes to 2 hours, and most preferably at a temperature of 483° C. for a period of 1 hour.

The catalyst precursor may then be activated to form the catalyst by reducing the metals of the non-support metal components to their metallic, zero-oxidation states. The catalyst precursor may be reduced to form the catalyst by holding the catalyst precursor under a hydrogen atmosphere at an elevated temperature. In an embodiment, the catalyst precursor may be held at a temperature of from 100° C. to 500° C. for a period of from 20 minutes to 24 hours to reduce the metals of the non-support metal components and activate the catalyst. The catalyst is preferably activated by heating the catalyst precursor under a flowing $H_2$ atmosphere. Most preferably, the catalyst is activated under flowing $H_2$ atmosphere by heating at a temperature ramped up from room temperature to 107° C. at 0.4° C. per minute, holding the catalyst precursor at 107° C. for 1 hour, ramping the temperature up from 107° C. to 399° C. at 0.9° C. per minute, holding the catalyst precursor at 399° C. for 4 hours, and cooling to room temperature.

The activated catalyst may be transferred to storage under an inert atmosphere and stored under liquid PDO or ethylene glycol prior to use.

In a preferred process of the present invention, HPA is the aldehyde to be hydrogenated, and is hydrogenated to form PDO. PDO may be prepared by hydrogenating an aqueous solution of HPA in the presence of the catalyst in accordance with the process of the present invention.

An aqueous solution of HPA may be prepared by a process involving the catalyzed hydroformylation (reaction with synthesis gas, $H_2/CO$) of ethylene oxide to form a dilute mixture of HPA in an organic solvent, typically methyl t-butyl ether (MTBE). The HPA in the organic solvent can be extracted into water to form a more concentrated HPA solution. U.S. Pat. No. 5,786,524 describes such a process wherein ethylene oxide and synthesis gas are contacted at 50° C. to 100° C. and at 3.44 MPa to 34.4 MPa in the presence of a cobalt or rhodium hydroformylation catalyst and a catalyst promoter to produce a product mixture containing HPA. Water is added to the HPA mixture and most of the HPA is extracted into the water to provide an aqueous phase comprising a higher concentration of HPA and an organic phase containing at least a portion of the hydroformylation catalyst.

Alternatively, an aqueous solution of HPA may be prepared by hydration of acrolein, as described in detail in U.S. Pat. No. 5,015,789. In that process, acrolein and water are reacted in a weight ratio of 1:2 to 1:20, preferably from 1:3 to 1:6, at 30° C. to 120° C., preferably at 50° C. to 90° C., and a pressure in a range from 0.1 MPa to 2.0 MPa, preferably 0.2 MPa to 0.5 MPa, in the presence of an acidic cation exchanger resin to form HPA. After production of HPA, the HPA solution is separated from the ion exchanger, preferably by sedimentation or filtration, and the reaction mixture is separated from unreacted acrolein to provide a concentrated aqueous solution of HPA. The separation of acrolein may be carried out by distillation under reduced pressure, preferably in a thin-layer evaporator.

However obtained, the aqueous solution of HPA may be supplied to at least one hydrogenation reactor containing the hydrogenation catalyst described above, preferably in a fixed-bed configuration, for hydrogenation to PDO. The preferred hydrogenation catalyst may contain from 3 wt. % to 7 wt. % nickel and from 2 wt. % to 3 wt. % molybdenum, by metallic weight, on a support containing at least 95 wt. % α-alumina. The catalyst may be formed in the shape of tri-lobal or cylindrical pellets.

The aqueous solution of HPA may contain HPA in a concentration in the range of 0.2 wt. % to 50 wt. %, based on the weight of the aqueous liquid, which is usually water or a combination of water and PDO. It is desirable to use a dilute solution of HPA with a fixed-bed catalyst, preferably having an HPA concentration of at most 15 wt. % HPA, more preferably having an HPA concentration of from 0.2 wt. % to 15 wt. %, and most preferably having an HPA concentration of at most 8 wt. %, particularly an HPA concentration of from 0.5 wt. % to 8 wt. %. Diffusion of $H_2$ through the fixed-bed catalyst is the rate limiting step in hydrogenating HPA to PDO, and the selectivity of hydrogenation of HPA to PDO is increased by utilizing an aqueous solution having a dilute concentration of HPA to ensure that HPA is catalyzed in the presence of $H_2$ to form PDO, rather than catalyzed to form undesirable side products in the absence of $H_2$.

Although any aqueous liquid that will not interfere with hydrogenation of HPA, including water, may be used to dilute the aqueous solution of HPA to the desired concentration, it is preferred to employ an aqueous PDO containing solution such as a portion of the product stream from the hydrogenation step. Dilution with such a PDO-containing solution serves to concentrate PDO in the system water, thus avoiding the high cost and recovery of dilute PDO from water which would result from the use of water alone as diluent.

The HPA in the dilute aqueous HPA solution may be reacted with hydrogen in the presence of the catalyst using methods known in the art. A fixed-bed hydrogenation reactor is preferred for conducting the hydrogenation on an industrial scale with the catalyst of the invention. In such a reactor, the liquid reaction mixture flows or trickles over the catalyst in a fixed-bed together with the hydrogen. To ensure good distribution of the hydrogen in the reaction mixture and uniform distribution of the gas/liquid mixture over the entire cross-section of the fixed bed, the liquid reaction mixture and hydrogen may be passed together through static mixers before the catalyst bed.

The hydrogenation process may be carried out in one stage or in two or more sequential stages. Generally, the hydrogenation may be carried out at a temperature of from 30° C. to 190° C. and at a hydrogen partial pressure of from 3.44 MPa to 68.9 MPa. In a preferred embodiment, hydrogenation is initially carried out at a temperature of from 40° C. to 90° C. and a hydrogen partial pressure of from 8.96 MPa to 10.3 MPa, followed by a second stage hydrogenation carried out at a temperature higher than that of the first stage and within the range of from 50° C. to 120° C. and a hydrogen partial pressure of from 7.56 MPa to 10.3 MPa, and then optionally in a third stage hydrogenation at a temperature greater than the temperature of the second stage and with a temperature of 120° C. or greater, preferably from 120° C. to 190° C. and a hydrogen partial pressure of from 6.89 MPa to 10.3 MPa. The second hydrogenation stage and any subsequent hydrogenation stages may be carried out at higher temperatures without negatively affecting selectivity since most of the HPA is hydrogenated in the first stage, and the solution has a very dilute concentration of HPA in the second and later hydrogenation stages. In this preferred process, the hydrogenation is optionally carried out in two or more separate hydrogenation vessels.

The hydrogenation reaction is preferably carried out at acidic conditions below pH 6.5 since HPA tends to form aldol condensation products and heavy end byproducts at higher pHs. Preferably the hydrogenation is carried out at a pH of from 4.0 to 6.5.

The hydrogenation reaction may be carried out in a batch process or in a continuous process. For industrial scale production of PDO from HPA it is preferred to utilize a continuous process.

The process of hydrogenating HPA to PDO of the present invention with the catalyst of the present invention provides a high degree and rate of conversion of HPA by hydrogenation, particularly over an extended period of time. HPA may be initially converted in the hydrogenation reaction at a rate of at least 50 ml HPA/ml catalyst.hr at a temperature of from 40° C. to 90° C., a pH of from 4.0 to 6.5, and a hydrogen partial pressure of from 6.89 MPa to 11.0 MPa. HPA may still be hydrogenated in the hydrogenation reaction with a high degree of activity after the catalyst is exposed to hydrogenation reaction conditions for an extended period of time. In an embodiment of the invention, HPA is hydrogenated at a rate of at least 30 ml HPA/ml catalyst.hr at a temperature of from 40° C. to 90° C., a pH of from 4.0 to 6.5, and a hydrogen partial pressure of from 6.89 MPa to 11.0 MPa after at least 24 hours exposure to HPA hydrogenation conditions. In another embodiment, HPA is hydrogenated at a rate of at least 35 ml HPA/ml catalyst.hr at a temperature of from 40° C. to 90° C., a pH of from 4.0 to 6.5, and a hydrogen partial pressure of from 6.89 MPa to 11.0 MPa after at least 24 hours of exposure to HPA hydrogenation conditions, and most preferably HPA is hydrogenated at a rate of at least 40 ml HPA/ml catalsyt.hr under such conditions after at least 24 hours of exposure to HPA hydrogenation conditions.

EXAMPLE 1

HPA was converted to PDO in accordance with the present invention using a catalyst comprising an α-alumina support with 5 wt. % nickel and 2 wt. % molybdenum deposited thereon, where the α-alumina support was comprised of at least 95% α-alumina.

The catalyst was prepared as follows. Gamma-alumina pellets were calcined at 1275° C. to prepare the α-alumina support. An aqueous nickel and molybdenum solution was prepared by dissolving 7.1 grams of ammonium carbonate in 20 ml of ammonium hydroxide solution (28-30%) with moderate heat and stirring, followed by the addition and dissolution of 3.9 grams of ammonium dimolybdate in the ammonium carbonate/ammonium hydroxide solution, after which 13.71 grams of nickel carbonate was added and dissolved in the ammonium carbonate/ammonium hydroxide/ammonium dimolybdate solution. The solution volume was brought to 40 ml with additional ammonium hydroxide solution (28-30%). 100 grams of the α-alumina support was impregnated with the solution containing the nickel and molybdenum, absorbing 100% of the solution volume. The nickel/molybdenum solution impregnated support was then aged for 1 hour at room temperature. The nickel/molybdenum impregnated support was then dried at 150° C. for 3 hours, and then calcined at 453° C. for 1 hour in air to produce a catalyst containing 5 wt. % nickel and 2 wt. % molybdenum.

Prior to use the catalyst was reduced under a flow of hydrogen gas. 50 grams of the catalyst was heated under a flow of hydrogen gas from room temperature to 107° C. at 0.4° C./minute and then held at 107° C. for 1 hour, after which the temperature was ramped to 399° C. at 0.9° C./minute and the catalyst was held at 399° C. for 4 hours. The catalyst was then cooled to room temperature and dropped into 1,3-propanediol without air contact.

The hydrogenation was conducted as follows. A 21 ml volume of the nickel/molybdenum catalyst, with a catalyst density of 0.62 g/cm³ and a void fraction of 0.42, was loaded into a batch hydrogenation wire basket to provide a catalyst charge of 13.1 grams, which was then topped with a ⅛ inch (0.32 cm) layer of inert denstone to prevent the catalyst from moving during the hydrogenation. The basket containing the catalyst was then secured in the cooling coils of a batch hydrogenation reactor. The catalyst was then rinsed three times with deionized nitrogen sparged water.

The catalyst was then subjected to 20 batch hydrogenation cycles, each cycle lasting for 120 minutes. Importantly, the catalyst was not renewed or refreshed between batches, so each batch sequentially aged the catalyst. Initially the reactor was loaded with 300 ml of an aqueous HPA/PDO feed mixture containing 1% n-butanol internal standard by weight, and after each batch cycle the hydrogenation reactor was drained through a dip tube then reloaded with 300 ml of aqueous HPA/PDO feed mixture. The feed mixture of aqueous HPA/PDO for the 20 batch hydrogenation cycles in Example 1 was mixed as shown in Table 1 below.

TABLE 1

| | Cycle | | | | | | | | | | | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| HPA (ml) | 60 | 60 | 60 | 60 | 150 | 150 | 150 | 150 | 150 | 150 | 150 | 150 | 150 | 150 | 150 | 150 | 60 | 60 | 60 | 60 |
| PDO/ $H_2O$ (ml) | 240 | 240 | 240 | 240 | 150 | 150 | 150 | 150 | 150 | 150 | 150 | 150 | 150 | 150 | 150 | 150 | 240 | 240 | 240 | 240 |
| Total (ml) | 300 | 300 | 300 | 300 | 300 | 300 | 300 | 300 | 300 | 300 | 300 | 300 | 300 | 300 | 300 | 300 | 300 | 300 | 300 | 300 |

The HPA content of the HPA portion of the feed mixture was between 5 wt. % and 30 wt. % prior to dilution with the PDO/$H_2O$ solution.

For each cycle, the loaded reactor was pressured with hydrogen to 2.07 MPa and then vented slowly three times to remove air from the system. The vented, loaded reactor was then pressured to a range of 5.5 MPa to 6.2 MPa with hydrogen. The temperature of the pressurized loaded reactor was then raised to 60° C. After the temperature of the reactor was stable at 60° C., the hydrogen pressure was increased to the final hydrogenation reaction pressure of 7.17 MPa. The hydrogenation reaction of each cycle was run for 120 minutes, and samples were taken of the reaction mixture at 0 minutes, 30 minutes, 60 minutes, and 120 minutes. The samples were analyzed by gas chromatograph for 3-hydroxypropionaldehyde and 1,3-propanediol in a solution of sample and tetrahydrofuran in a ratio, by volume, of sample to THF of 1:5. Kinetics were determined by the rate of disappearance of HPA.

The initial HPA content, final HPA content, and amount of HPA converted by the catalyst are shown in Table 2. Table 2 also shows the HPA conversion rate initially and the average HPA conversion rate for cycles 13-15 (catalyst activity after 24 hours of exposure to hydrogenation conditions, for hours 24-30). Finally, Table 2 shows the initial PDO content and the final PDO content of each cycle.

TABLE 2

| Cycle | Initial HPA (wt. %) | Final HPA (wt. %) | HPA converted (g) | HPA conversion rate (ml/ml · hr) | Average HPA conversion rate cycles 13-15 (ml/ml · hr) | Initial PDO (wt. %) | Final PDO (wt. %) |
|---|---|---|---|---|---|---|---|
| 1 | 3.03 | 0.00 | 9.09 | >50 | — | 19.5 | 23.8 |
| 2 | 2.63 | 0.00 | 7.90 | >50 | — | 19.7 | 24.0 |
| 3 | 2.61 | 0.01 | 7.80 | 72.3 | — | 20.2 | 23.6 |
| 4 | 2.80 | 0.01 | 8.37 | 68.6 | — | 21.6 | 25.1 |
| 5 | 7.31 | 0.21 | 21.3 | 51.2 | — | 14.3 | 23.2 |
| 6 | 7.22 | 0.40 | 20.5 | 41.2 | — | 14.4 | 23.4 |
| 7 | 7.40 | 0.57 | 20.5 | 36.1 | — | 14.7 | 22.8 |
| 8 | 7.85 | 0.58 | 21.8 | 37.4 | — | 15.0 | 24.2 |
| 9 | 6.61 | 0.33 | 18.8 | 44.6 | — | 14.4 | 23.9 |
| 10 | 6.94 | 0.50 | 19.3 | 37.0 | — | 14.3 | 22.2 |
| 11 | 6.92 | 0.67 | 18.8 | 33.0 | — | 14.8 | 22.3 |
| 12 | 6.64 | 0.73 | 17.7 | 31.7 | — | 15.1 | 23.9 |
| 13 | 6.57 | 0.56 | 18.0 | 35.6 | 33.5 | 14.3 | 22.7 |
| 14 | 6.88 | 0.59 | 18.9 | 34.3 | 33.5 | 14.0 | 22.0 |
| 15 | 7.00 | 0.77 | 18.7 | 30.5 | 33.5 | 14.1 | 22.2 |
| 16 | 7.50 | 0.92 | 19.7 | 29.9 | — | 15.2 | 24.0 |
| 17 | 2.32 | 0.00 | 7.0 | — | — | 20.0 | 24.0 |
| 18 | 2.33 | 0.00 | 7.0 | — | — | 19.9 | 24.6 |
| 19 | 2.30 | 0.00 | 6.9 | — | — | 20.2 | 23.5 |
| 20 | 2.76 | 0.00 | 8.29 | — | — | 23.58 | 26.81 |

As shown in Table 2, the nickel/molybdenum catalyst is highly effective for converting HPA at a high activity rate over the entire set of batches. As shown by the initial PDO and final PDO measurements in Table 2, HPA was converted substantially into PDO.

EXAMPLE 2

HPA was converted to PDO in accordance with the present invention using a catalyst comprising an α-alumina support with 5 wt. % nickel, 2 wt. % molybdenum, and 0.5 wt. % cobalt deposited thereon, where the α-alumina support was comprised of at least 95% α-alumina.

The catalyst was prepared as follows. Gamma-alumina pellets were calcined at 1275° C. to prepare the α-alumina support. An aqueous nickel/molybdenum/cobalt solution was prepared by dissolving 3.6 grams of ammonium carbonate in 12 ml of ammonium hydroxide solution (28-30%) with moderate heat and stirring, followed by the addition and dissolution of 2.0 grams of ammonium dimolybdate in the ammonium carbonate/ammonium hydroxide solution, after which 6.9 grams of nickel carbonate was added and dissolved in the ammonium carbonate/ammonium hydroxide/ammonium dimolybdate solution, and then 0.6 grams of cobalt carbonate was added and dissolved therein. The solution volume was brought to 20 ml with additional ammonium hydroxide solution (28-30%). 50 grams of the α-alumina support was impregnated with the solution containing the nickel, molybdenum and cobalt, absorbing 100% of the solution volume. The nickel/molybdenum/cobalt solution impregnated support was then aged for 1 hour at room temperature. The nickel/molybdenum/cobalt impregnated support was then dried at 150° C. for 3 hours, and then calcined at 453° C. for 1 hour in air to produce a catalyst containing 5 wt. % nickel, 2 wt. % molybdenum, and 0.5 wt. % cobalt.

Prior to use the catalyst was reduced under a flow of hydrogen gas as described above in Example 1.

The hydrogenation was conducted in the same manner as set forth in Example 1 for 20 cycles. The initial HPA content, final HPA content, and amount of HPA converted by the catalyst are shown in Table 3. Table 3 also shows the HPA conversion rate initially and the average HPA conversion rate for cycles 13-15 (catalyst activity after 24 hours of exposure to hydrogenation conditions, for hours 24-30). Finally, Table 3 shows the initial PDO content and the final PDO content of each cycle.

TABLE 3

| Cycle | Initial HPA (wt. %) | Final HPA (wt. %) | HPA converted (g) | HPA conversion rate (ml/ml · hr) | Average HPA conversion rate cycles 13-15 (ml/ml · hr) | Initial PDO (wt. %) | Final PDO (wt. %) |
|---|---|---|---|---|---|---|---|
| 1 | 3.85 | 0.00 | 11.6 | >50 | — | 18.3 | 19.9 |
| 2 | 3.38 | 0.00 | 10.1 | >50 | — | 15.9 | 18.8 |
| 3 | 3.40 | 0.00 | 10.2 | >50 | — | 17.6 | 18.8 |
| 4 | 3.51 | 0.00 | 10.5 | >50 | — | 18.1 | 19.9 |
| 5 | 8.80 | 0.89 | 23.7 | 32.1 | — | 13.9 | 19.5 |
| 6 | 9.00 | 1.35 | 23.0 | 25.8 | — | 14.0 | 19.5 |
| 7 | 9.17 | 1.78 | 22.2 | 22.2 | — | 14.2 | 19.9 |
| 8 | 9.48 | 2.03 | 22.4 | 20.8 | — | 14.6 | 19.9 |
| 9 | 9.11 | 1.93 | 21.6 | 21.4 | — | 14.0 | 18.4 |
| 10 | 9.01 | 2.34 | 20.0 | 17.8 | — | 13.9 | 17.8 |
| 11 | 9.33 | 2.43 | 20.7 | 18.0 | — | 13.7 | 18.2 |
| 12 | 9.79 | 2.42 | 22.1 | 18.3 | — | 14.3 | 18.4 |

TABLE 3-continued

| Cycle | Initial HPA (wt. %) | Final HPA (wt. %) | HPA converted (g) | HPA conversion rate (ml/ml · hr) | Average HPA conversion rate cycles 13-15 (ml/ml · hr) | Initial PDO (wt. %) | Final PDO (wt. %) |
|---|---|---|---|---|---|---|---|
| 13 | 9.92 | 2.50 | 22.3 | 18.0 | 16.8 | 14.3 | 19.6 |
| 14 | 9.84 | 2.76 | 21.2 | 16.6 | 16.8 | 14.4 | 19.2 |
| 15 | 9.87 | 2.91 | 20.9 | 15.9 | 16.8 | 14.2 | 18.3 |
| 16 | 10.15 | 3.08 | 21.2 | 16.2 | — | 14.6 | 18.9 |
| 17 | 3.90 | 0.21 | 11.1 | — | — | 16.6 | 20.0 |
| 18 | 3.36 | 0.13 | 9.7 | — | — | 17.9 | 18.5 |
| 19 | 3.41 | 0.09 | 10.0 | — | — | 18.5 | 19.0 |
| 20 | 3.49 | 0.08 | 10.2 | — | — | 18.0 | 18.8 |

As shown in Table 3, the nickel/molybdenum/cobalt catalyst is effective for converting HPA at a relatively high activity rate over the entire set of batches. As shown by the intial PDO and final PDO measurements in Table 3, HPA was converted substantially into PDO.

EXAMPLE 3

For comparative purposes, HPA was converted to PDO with a catalyst comprising an α-alumina support with 5 wt. % nickel deposited thereon, a process not in accordance with the present invention, where the α-alumina support was comprised of at least 95% α-alumina.

The catalyst was prepared as follows. Gamma-alumina pellets were calcined at 1275° C. to prepare the α-alumina support. An aqueous nickel solution was prepared by dissolving 6.9 grams of ammonium carbonate in 20 ml of ammonium hydroxide solution (28-30%) with moderate heat and stirring, followed by the addition and dissolution of 13.3 grams of nickel carbonate in the ammonium carbonate/ammonium hydroxide solution. The solution volume was brought to 40 ml with additional ammonium hydroxide solution (28-30%). 100 grams of the α-alumina support was impregnated with the nickel solution, absorbing 100% of the solution volume. The nickel solution impregnated support was then aged for 1 hour at room temperature. The nickel impregnated support was then dried at 150° C. for 3 hours, and then calcined at 453° C. for 1 hour in air to produce a catalyst containing 5 wt. % nickel.

Prior to use the catalyst was reduced as set forth in Example 1. HPA was hydrogenated to PDO in accordance with the procedure set forth in Example 1 using the nickel catalyst rather than the nickel/molybdenum catalyst. A 21 ml volume of the catalyst (12.1 grams) was used with a catalyst density of 0.58 g/cm$^3$ and a void fraction of 0.42

The initial HPA content, final HPA content, and amount of HPA converted by the catalyst are shown in Table 4. Table 4 also shows the HPA conversion rate initially and the average HPA conversion rate for cycles 13-15 (catalyst activity after 24 hours of exposure to hydrogenation conditions, for hours 24-30). Finally, Table 4 shows the initial PDO content and the final PDO content of each cycle.

TABLE 4

| Cycle | Initial HPA (wt. %) | Final HPA (wt. %) | HPA converted (g) | HPA conversion rate (ml/ml · hr) | Average HPA conversion rate cycles 13-15 (ml/ml · hr) | Initial PDO (wt. %) | Final PDO (wt. %) |
|---|---|---|---|---|---|---|---|
| 1 | 3.53 | 0.00 | 10.58 | >50 | — | 19.5 | 23.9 |
| 2 | 3.10 | 0.00 | 9.31 | >50 | — | 20.4 | 23.7 |
| 3 | 3.09 | 0.65 | 7.32 | 20.59 | — | 20.9 | 23.3 |
| 4 | 3.21 | 1.21 | 6.00 | 12.98 | — | 21.5 | 23.63 |
| 5 | 8.33 | 6.48 | 5.56 | 3.61 | — | 15.9 | 17.7 |
| 6 | 9.52 | 7.62 | 5.71 | 2.77 | — | 15.4 | 16.4 |
| 7 | 9.67 | 8.09 | 4.74 | 2.15 | — | 15.2 | 15.4 |
| 8 | 10.47 | 8.97 | 4.50 | 2.56 | — | 16.0 | 16.2 |
| 9 | 9.48 | 8.58 | 2.69 | 1.49 | — | 15.5 | 15.9 |
| 10 | 9.36 | 8.57 | 2.37 | 0.89 | — | 14.6 | 14.7 |
| 11 | 9.38 | 8.76 | 1.88 | 1.33 | — | 14.2 | 14.7 |
| 12 | 10.12 | 9.63 | 1.48 | 0.53 | — | 15.3 | 15.7 |
| 13 | 9.49 | 9.01 | 1.44 | 1.00 | 2.1 | 14.6 | 14.9 |
| 14 | 9.66 | 7.86 | 5.40 | 3.03 | 2.1 | 14.5 | 12.7 |
| 15 | 9.66 | 8.21 | 4.33 | 2.33 | 2.1 | 14.5 | 13.4 |
| 16 | 10.52 | 10.11 | 1.22 | 0.16 | — | 15.8 | 15.6 |
| 17 | 4.58 | 4.24 | 0.99 | 0.74 | — | 19.6 | 19.4 |
| 18 | 3.71 | 3.56 | 0.44 | 0.51 | — | 19.7 | 20.5 |
| 19 | 3.70 | 3.35 | 1.06 | 1.10 | — | 20.8 | 20.3 |
| 20 | 3.79 | 3.78 | 0.04 | 0.54 | — | 21.1 | 22.7 |

As shown in Table 4, particularly in comparison with Tables 2 and 3, the 5 wt. % nickel catalyst was not as effective for converting HPA at a high activity rate over the entire set of batches as the catalyst used in Example 1 or Example 2.

EXAMPLE 4

For comparative purposes, HPA was converted to PDO in accordance with a method not of the present invention using a catalyst comprising an α-alumina support with 5 wt. % nickel and 2 wt. % tungsten deposited thereon, where the α-alumina support was comprised of at least 95% α-alumina.

The catalyst was prepared as follows. Gamma-alumina pellets were calcined at 1275° C. to prepare the α-alumina support. An aqueous nickel and tungsten solution was prepared by dissolving 7.1 grams of ammonium carbonate in 20 ml of ammonium hydroxide solution (28-30%) with moderate heat and stirring, followed by the addition and dissolution of 13.6 grams of nickel carbonate in the ammonium carbonate/ammonium hydroxide solution, after which 3.0 grams of ammonium meta tungstate was added and dissolved in the ammonium carbonate/ammonium hydroxide/nickel carbonate solution. The solution volume was brought to 40 ml with additional ammonium hydroxide solution (28-30%). 100 grams of the α-alumina support was impregnated with the solution containing the nickel and tungsten, absorbing 100% of the solution volume. The nickel/tungsten solution impregnated support was then aged for 1 hour at room temperature. The nickel/tungsten impregnated support was then dried at 150° C. for 3 hours, and then calcined at 453° C. for 1 hour in air to produce a catalyst containing 5 wt. % nickel and 2 wt. % tungsten.

Prior to use the catalyst was reduced under a flow of hydrogen gas as described above in Example 1. The hydrogenation was conducted in the same manner for 20 cycles as set forth in Example 1, except the catalyst had a catalyst density of 0.57 g/cm$^3$ and a void fraction of 0.42, and the 21 ml volume of catalyst provided a catalyst charge of 11.9 grams.

The initial HPA content, final HPA content, and amount of HPA converted by the catalyst are shown in Table 5. Table 5 also shows the HPA conversion rate initially and the average HPA conversion rate for cycles 13-15 (catalyst activity after 24 hours of exposure to hydrogenation conditions, for hours 24-30). Finally, Table 5 shows the initial PDO content and the final PDO content of each cycle.

TABLE 5

| Cycle | Initial HPA (wt. %) | Final HPA (wt. %) | HPA converted (g) | HPA conversion rate (ml/ml · hr) | Average HPA conversion rate cycles 13-15 (ml/ml · hr) | Initial PDO (wt. %) | Final PDO (wt. %) |
|---|---|---|---|---|---|---|---|
| 1 | 3.26 | 0.00 | 9.8 | >50 | — | 19.5 | 23.3 |
| 2 | 2.83 | 0.00 | 8.5 | >50 | — | 19.2 | 21.8 |
| 3 | 3.09 | 0.17 | 8.8 | 39.9 | — | 21.1 | 23.3 |
| 4 | 3.13 | 0.38 | 8.3 | 28.1 | — | 21.8 | 23.3 |
| 5 | 7.69 | 3.73 | 11.9 | 9.2 | — | 15.6 | 18.8 |
| 6 | 8.30 | 5.25 | 9.2 | 5.7 | — | 14.6 | 16.9 |
| 7 | 8.82 | 6.41 | 7.2 | 4.3 | — | 14.6 | 16.7 |
| 8 | 9.48 | 7.33 | 6.4 | 2.8 | — | 15.3 | 16.4 |
| 9 | 8.66 | 7.49 | 3.5 | 1.6 | — | 14.4 | 14.9 |
| 10 | 8.66 | 7.95 | 1.8 | 1.1 | — | 13.3 | 14.5 |
| 11 | 9.16 | 8.13 | 3.1 | 1.5 | — | 14.0 | 14.8 |
| 12 | 9.99 | 8.63 | 4.1 | 1.6 | — | 14.9 | 15.5 |
| 13 | 8.86 | 7.91 | 2.9 | 1.4 | 1.3 | 14.6 | 15.0 |
| 14 | 9.11 | 8.18 | 2.8 | 1.1 | 1.3 | 14.0 | 14.2 |
| 15 | 9.00 | 8.17 | 2.5 | 1.3 | 1.3 | 13.9 | 14.6 |
| 16 | 9.58 | 8.73 | 2.6 | 1.1 | — | 14.6 | 15.1 |
| 17 | 4.29 | 3.75 | 1.6 | 1.4 | — | 18.7 | 18.6 |
| 18 | 3.45 | 3.02 | 1.3 | 1.9 | — | 19.0 | 19.3 |
| 19 | 3.31 | 2.91 | 1.2 | 1.3 | — | 19.2 | 19.6 |
| 20 | 3.35 | 2.97 | 1.1 | 1.5 | — | 19.2 | 20.1 |

As shown in Table 5, particularly in comparison with Tables 2 and 3, the 5 wt. % nickel and 2 wt. % tungsten catalyst was not as effective for converting HPA at a high activity rate over the entire set of batches as the catalyst used in Example 1 or Example 2.

What is claimed is:

1. A process for hydrogenating an aldehyde, comprising: contacting an aldehyde with a catalyst in the presence of hydrogen where the catalyst is comprised of a support and non-support metal components dispersed on the surface of the support, the support containing at least about 95% α-alumina as measured by powder x-ray diffraction, and the non-support metal components comprise nickel and/or one or more compounds thereof and molybdenum and/or one or more compounds thereof, where the nickel and/or one or more compounds thereof comprises from about 3 wt. % to about 9 wt. % of the catalyst, by metallic weight, and the molybdenum and/or one or more compounds thereof comprises from about 1 wt. % to about 4 wt. %, by metallic weight, of the catalyst.

2. The process of claim 1 wherein non-support metal components other than nickel and molybdenum comprise up to about 1 wt. % of the catalyst, by metallic weight.

3. The process of claim 1 wherein the non-support metal components do not include ruthenium, platinum, or palladium.

4. The process of claim 1 wherein the non-support metal components consist essentially of nickel and/or one or more compounds thereof and molybdenum and/or one or more compounds thereof.

5. The process of claim 1 wherein the catalyst has a N$_2$ BET surface area of from about 12 m$^2$/g to about 30 m$^2$/g.

6. The process of claim 1 wherein the catalyst has a pore size distribution having a median pore diameter of from about 1300 Å to about 1700 Å as measured by mercury porosimetry at a 140° contact angle.

7. The process of claim 1 wherein the nickel content of the catalyst, by metallic weight, is equal to or greater than the molybdenum content of the catalyst, by metallic weight.

8. The process of claim 1 wherein the weight ratio of nickel to molybdenum, by metallic weight, is from about 1:1 to about 3:1.

9. The process of claim 1 wherein the catalyst has a crush strength of at least about 2.3 kg/mm.

10. The process of claim 1 wherein the catalyst support is comprised of at most about 0.6 wt. % silica as measured by x-ray fluorescence.

11. The process of claim 1 wherein the aldehyde is a hydroxyaldehyde.

12. The process of claim 11 wherein the hydroxyaldehyde is 3-hydroxypropionaldehyde.

13. The process of claim 12 wherein the catalyst has an activity sufficient to convert 3-hydroxypropionaldehyde at a rate of at least 30 ml 3-hydroxypropionaldehyde/catalyst ml.hr at a temperature of from 50° C. to 90° C. at a pH of from 4.0 to 6.5, and at a hydrogen partial pressure of from 6.9 MPa to 11 MPa after at least 24 hours of catalyzing hydrogenation of 3-hydroxypropionaldehyde at a temperature of from 50° C. to 90° C., at a pH of from 4.0 to 6.5, and at a hydrogen partial pressure of from 6.9 MPa to 11 MPa.

14. The process of claim 12 wherein the 3-hydroxypropionaldehyde is in an aqueous solution where the 3-hydroxypropionaldehyde comprises at most about 15 wt. % of the aqueous solution.

15. The process of claim 12 wherein the 3-hydroxypropionaldehyde is hydrogenated to 1,3-propanediol under a hydrogen partial pressure of from about 6.9 MPa to about 11 MPa, at a temperature of from about 40° C. to about 190° C., and at a pH of less than about 6.5.

16. The process of claim 1 wherein the aldehyde is hydrogenated under a hydrogen partial pressure of from about 6.9 MPa to about 11 MPa, at a temperature of from about 40° C. to about 190° C., and at a pH of less than about 6.5.

17. The process of claim 1 wherein the catalyst further comprises from about 0.1 wt. % to about 1 wt. % cobalt and/or one or more compounds thereof, by metallic weight.

18. The process of claim 1 wherein the catalyst comprises at most about 8 wt. % nickel and molybdenum by combined metallic weight.

19. The process of claim 1 wherein the aldehyde is contacted with the catalyst in the presence of hydrogen at a pH of at most about 6.5.

20. The process of claim 1 wherein the aldehyde is contacted with the catalyst in the presence of hydrogen at a temperature of from about 40° C. to about 190° C.

21. The process of claim 1, wherein the aldehyde is provided for contact with the catalyst by converting an acetal to the aldehyde.

22. The process of claim 21 wherein the acetal is present in a hydrogenation reaction product.

* * * * *